(12) United States Patent
Wen

(10) Patent No.: US 11,964,094 B2
(45) Date of Patent: Apr. 23, 2024

(54) METHOD AND APPARATUS FOR IRRIGATION

(71) Applicant: Medtronic Xomed, Inc., Jacksonville, FL (US)

(72) Inventor: Jie Wen, St. Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 17/480,862

(22) Filed: Sep. 21, 2021

(65) Prior Publication Data

US 2022/0072219 A1 Mar. 10, 2022

Related U.S. Application Data

(63) Continuation of application No. 15/332,693, filed on Oct. 24, 2016, now abandoned, which is a
(Continued)

(51) Int. Cl.
| | |
|---|---|
| *A61M 1/00* | (2006.01) |
| *A61B 90/70* | (2016.01) |
| *A61M 3/02* | (2006.01) |
| *A61M 5/14* | (2006.01) |
| *A61M 5/142* | (2006.01) |

(Continued)

(52) U.S. Cl.
CPC ............... *A61M 1/77* (2021.05); *A61B 90/70* (2016.02); *A61M 1/81* (2021.05); *A61M 1/85* (2021.05); *A61M 3/0262* (2013.01); *A61M 3/0283* (2013.01); *A61M 5/1413* (2013.01); *A61M 5/14216* (2013.01); *A61M 5/1424* (2013.01); *A61M 11/007* (2014.02); *A61M 39/10* (2013.01); *A61M 39/24* (2013.01); *B08B 3/04* (2013.01); *A61M 2039/2493* (2013.01); *A61M 2210/0618* (2013.01); *A61M 2210/0681* (2013.01)

(58) Field of Classification Search
CPC .... A61M 1/77; A61M 3/0262; A61M 3/0283; A61M 39/24
See application file for complete search history.

(56) References Cited

U.S. PATENT DOCUMENTS

| | | | | |
|---|---|---|---|---|
| 1,496,126 A | * | 6/1924 | Livingstone | ........ A61M 3/0262 |
| | | | | 222/372 |
| 1,644,225 A | | 10/1927 | Barth | |

(Continued)

FOREIGN PATENT DOCUMENTS

| | | |
|---|---|---|
| AU | 2015200049 A1 | 2/2015 |
| CN | 102105183 A | 6/2011 |

(Continued)

OTHER PUBLICATIONS

Office Action dated Nov. 16, 2021, in corresponding Chinese Application No. 201680073548.6.
(Continued)

*Primary Examiner* — Brandy S Lee
*Assistant Examiner* — Hong-Van N Trinh
(74) *Attorney, Agent, or Firm* — Harness, Dickey & Pierce, P.L.C.

(57) ABSTRACT

Disclosed is an irrigation system. The irrigation system includes a manual pump. The manual pump can provide pressurized liquid through a tube at an outlet.

18 Claims, 5 Drawing Sheets

Related U.S. Application Data continuation-in-part of application No. 14/928,066, filed on Oct. 30, 2015, now Pat. No. 11,266,776.

(51) Int. Cl.
*A61M 11/00* (2006.01)
*A61M 39/10* (2006.01)
*A61M 39/24* (2006.01)
*B08B 3/04* (2006.01)

(56) References Cited

U.S. PATENT DOCUMENTS

| | | | |
|---|---|---|---|
| 3,214,775 | A | 11/1965 | Murov et al. |
| 3,452,745 | A | 7/1969 | Hutchinson et al. |
| 4,990,140 | A | 2/1991 | Black |
| 5,024,228 | A | 6/1991 | Goldstone et al. |
| 5,254,086 | A | 10/1993 | Palmer et al. |
| 5,264,260 | A | 11/1993 | Saab |
| 5,336,170 | A | 8/1994 | Salerno et al. |
| 5,358,473 | A * | 10/1994 | Mitchell ............. A61F 9/00736 604/27 |
| 5,591,135 | A * | 1/1997 | Sullivan ............. A61M 5/31581 604/207 |
| 5,599,576 | A | 2/1997 | Opolski |
| 5,720,719 | A | 2/1998 | Edwards et al. |
| 5,749,357 | A | 5/1998 | Linder |
| 5,766,158 | A | 6/1998 | Opolski |
| 5,807,340 | A | 9/1998 | Pokras |
| 5,968,017 | A | 10/1999 | Lampropoulos et al. |
| 6,200,292 | B1 * | 3/2001 | French ................ A61M 1/85 604/35 |
| 6,543,452 | B1 | 4/2003 | Lavigne |
| 6,843,432 | B1 | 1/2005 | Philpott |
| 7,361,168 | B2 | 4/2008 | Makower et al. |
| 7,410,480 | B2 | 8/2008 | Muni et al. |
| 7,419,497 | B2 | 9/2008 | Muni et al. |
| 7,462,175 | B2 | 12/2008 | Chang et al. |
| 8,206,349 | B2 | 6/2012 | Slenker et al. |
| 8,277,503 | B2 | 10/2012 | Lavigne |
| 8,594,805 | B2 | 11/2013 | Hincapie Ordonez et al. |
| 8,790,301 | B2 | 7/2014 | Slenker et al. |
| 9,037,226 | B2 | 5/2015 | Hacker et al. |
| 9,351,750 | B2 | 5/2016 | Muni et al. |
| 9,408,756 | B2 | 8/2016 | Jenkins et al. |
| 9,408,955 | B2 | 8/2016 | Jenkins et al. |
| 9,827,367 | B2 * | 11/2017 | Perry ................ A61M 3/0258 |
| 2004/0176738 | A1 * | 9/2004 | Paul .................... A61M 1/77 604/506 |
| 2004/0254522 | A1 | 12/2004 | Kraus et al. |
| 2006/0095066 | A1 | 5/2006 | Chang et al. |
| 2008/0183128 | A1 | 7/2008 | Morriss et al. |
| 2008/0289635 | A1 | 11/2008 | Hull |
| 2009/0270796 | A1 | 10/2009 | Perry et al. |
| 2010/0106108 | A1 * | 4/2010 | Hirsch .................. A61M 1/92 604/290 |
| 2010/0114016 | A1 | 5/2010 | Gallo et al. |
| 2011/0009699 | A1 | 1/2011 | Slenker et al. |
| 2011/0112512 | A1 | 5/2011 | Muni et al. |
| 2013/0053926 | A1 | 2/2013 | Hincapie Ordonez et al. |
| 2013/0072958 | A1 | 3/2013 | Ressemann et al. |
| 2013/0184574 | A1 | 7/2013 | Newhauser, Jr. et al. |
| 2013/0274600 | A1 * | 10/2013 | Jenkins ............. A61M 25/0152 600/431 |
| 2014/0014869 | A1 | 1/2014 | Fink et al. |
| 2014/0180138 | A1 | 6/2014 | Freeman et al. |
| 2014/0276625 | A1 | 9/2014 | Jenkins et al. |
| 2014/0276654 | A1 | 9/2014 | Jenkins |
| 2014/0363801 | A1 | 12/2014 | Samosky et al. |
| 2015/0088029 | A1 | 3/2015 | Wybo |
| 2015/0133779 | A1 | 5/2015 | Yurek et al. |
| 2016/0038072 | A1 | 2/2016 | Brown et al. |
| 2016/0038073 | A1 | 2/2016 | Brown et al. |
| 2017/0119952 | A1 | 5/2017 | Wen |
| 2017/0119953 | A1 | 5/2017 | Wen |
| 2018/0042524 | A1 | 2/2018 | Inman et al. |

FOREIGN PATENT DOCUMENTS

| | | |
|---|---|---|
| JP | H0646666 A | 2/1994 |
| JP | H08509636 A | 10/1996 |
| JP | 2000511804 A | 9/2000 |
| JP | 2001519212 A | 10/2001 |
| JP | 2006-528906 A | 12/2006 |
| JP | 2011518643 A | 6/2011 |
| JP | 2011-520563 A | 7/2011 |
| WO | 9424969 A1 | 11/1994 |
| WO | 9746161 A1 | 12/1997 |
| WO | 9919008 A1 | 4/1999 |
| WO | 2007134101 A2 | 11/2007 |
| WO | 2009134577 A1 | 11/2009 |
| WO | 2015143388 A1 | 9/2015 |
| WO | 2016064870 A1 | 4/2016 |

OTHER PUBLICATIONS

BD Cornwall—305224 "Fluid Dispensing Syringe" 2 pages; date accesssed: Aug. 30, 2016 at website: http://catalog.bd.com/nexus-ecat/getProductDetail?productId-305224.

Medtronic "Hydrodebrider Endoscopic Sinus Irrigation System" date accessed: Oct. 22, 2015 at website: http://www.medtronic.com//for-healthcare-professionals/products-therapies/ear-nose-throat/powered-ent-instruments/hydrodebrider-endoscopic-sinus-irrigation-system/.

Qosina 80187 "Dual Check Valve" 2 pages; date accesed: Oct. 30, 2015 at website: http://www.qosina.com/dual-check-valve-male-luer-lock-outlet-port-female-luer-slip-inlet-port-and-female-luer-lock-control-port-80187.

International Search Report and Written Opinion dated Mar. 21, 2017 for PCT/US2016/058871 claiming benefit of U.S. Appl. No. 14/928,066, filed Oct. 30, 2015 and U.S. Appl. No. 15/332,693, filed Oct. 24, 2016.

Invitation to Pay Additional Fees dated Jan. 25, 2017 for PCT/US2016/058871 claiming benefit of U.S. Appl. No. 14/928,066, filed Oct. 30, 2015 and U.S. Appl. No. 15/332,693, filed Oct. 24, 2016.

International Preliminary Report on Patentability dated May 11, 2018 in corresponding International Application No. PCT/US2016/058871.

International Search Report and Written Opinion dated Nov. 14, 2017 in corresponding International Application No. PCT/US2017/046312.

Schneider et al. "Continuous intraoperative vagus nerve stimulation for identification of imminent recurrent laryngeal nerve injury: Continuous IONM for Thyroid Surgery", Head and Neck, vol. 35, No. 11, Nov. 1, 2013, pp. 1591-1598, XP055421596, US ISSN: 1043-3074, DOI 10.1002/hed.23187.

MEMS Enable Medical Innovation by Mouser Electronics, Inc. May 4, 2015.

International Preliminary Report on Patentability dated Feb. 21, 2019 in corresponding International Application No. PCT/US2017/046312.

Office Action dated May 28, 2020 in corresponding/related Chinese Application No. 201680073548.6.

Examination Report dated Jul. 9, 2020 in corresponding/related Australian Application No. 2016346327.

Office Action dated May 25, 2020 in corresponding/related European Application No. 16790856.5.

Office Action dated Nov. 9, 2020 in corresponding/related Japanese Application No. 2018-522030.

Second Office Action regarding corresponding Chinese Application No. 201680073548.6, dated Apr. 6, 2021.

Office Action regarding Japanese Patent Application No. 2018-522030 (with English Translation), dated Apr. 30, 2021.

European Patent Office Official Letter corresponding to EP16790856.5 Dated Jan. 18, 2023.

* cited by examiner

METHOD AND APPARATUS FOR IRRIGATION

CROSS-REFERENCE TO RELATED APPLICATIONS

This application is a continuation of U.S. patent application Ser. No. 15/332,693 filed on Oct. 24, 2016; which is a continuation-in-part of U.S. patent application Ser. No. 14/928,066 filed on Oct. 30, 2015. The entire disclosure of the above applications are incorporated herein by reference.

FIELD

The subject disclosure relates to an irrigation system, and particularly relates to a manually powered irrigation system having a nozzle.

BACKGROUND

This section provides background information related to the present disclosure which is not necessarily prior art.

During selected procedures, it may be selected to provide a liquid to a specific location. Generally, fluid may be delivered through a tube that may be powered by a pump. Further, the tube may include suction portions to withdraw/remove material and/or irrigation liquid from a site. Selected systems include a Hydrodebrider® pressurized sinus irrigation system sold by Medtronic, Inc. and systems such as those disclosed in U.S. Patent Application Publication Nos. 2009/0270796 and 2011/0009699 and U.S. Pat. Nos. 8,790,301 and 8,206,349. Such systems are disclosed to include a vacuum source and a control to control a vacuum and irrigation.

SUMMARY

This section provides a general summary of the disclosure, and is not a comprehensive disclosure of its full scope or all of its features.

According to various embodiments, a manual pump may be fitted with a valve system. The manual pump may include a syringe or other hand-held and/or operated pump mechanism. The valve system may allow for unidirectional or one-directional delivery of a fluid.

The valve system may include two one-way valves to allow for filling of a syringe barrel during a first movement of a syringe piston and delivery of a liquid from the filled barrel during a second motion of the piston. The valve system, therefore, allows for generally continuous delivery of a fluid from a source to a selected area while connected to a source.

Delivery of the fluid may be through a nozzle to provide a selected pressure of fluid to an irrigation site. Irrigation sites may include both living and non-living sites. Living tissue or anatomical sites may include body surfaces, such as nasal and sinus cavities. Non-living sites may include cleaning or preparing surgical equipment, implants, or work surfaces, such as degreasing. During irrigation, the pressure may assist in loosening or removing a selected material from a selected surface or breaking up large agglomerations of material into smaller portions for removal.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
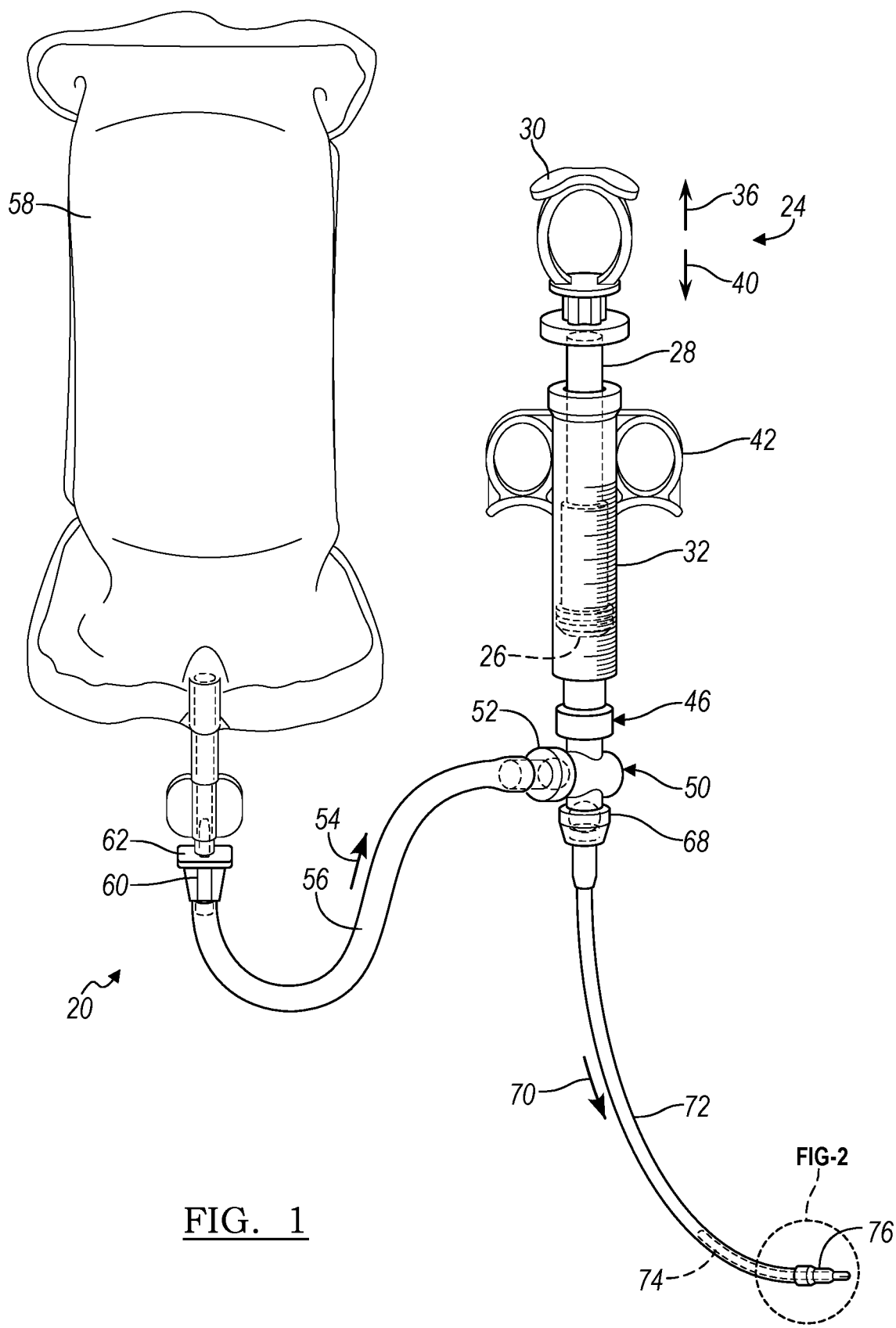
FIG. 1 is a plan view of an irrigation system, according to various embodiments.

With initial reference to FIG. 1, an irrigation system 20 is illustrated. The irrigation system 20 is generally a manual irrigation system powered by a user that holds a syringe assembly 24 in one or more hands to operate the syringe assembly 24. The syringe assembly 24 may include a piston head 26 interconnected with a piston rod 28. The piston rod 28 may include various features such as a thumb hole or loop 30 to assist in operation of the syringe assembly 24 with one hand of a human user.

The syringe assembly 24 may be a manual pump that may include various features such as further including finger or digit rings 42 to assist in manipulating the syringe assembly 24, in addition to the thumb hole or loop 30, again with one hand of a human user. Further, a connection portion 46 may include connection mechanisms such as a Luer-Lok® syringe connection, twist lock, press fit, or the like. Therefore, a mechanism may be interconnected with the syringe assembly 24 for use of the irrigation system 20.

As is generally understood by one skilled in the art, the syringe assembly 24 may be operated to fill a syringe barrel 32 by moving the piston head 26 with the piston rod 28 generally in the direction of arrow 36 and may be emptied by moving the piston head 26 with the piston rod 28 generally in the direction of arrow 40. It is understood, however, that the syringe assembly 24 may also have a self-return or self-priming system. Self-return systems may include a spring (not illustrated) to bias the piston head 26 away from the connection portion 46 generally in the direction of arrow 36. The user, to express the material from the syringe, would overcome the biasing force of the spring to express the material and the biasing force would assist in moving or move the piston head away from the connection portion 46 to refill the syringe barrel.

Connected with the syringe assembly 24 at the connection portion 46 may be a valve assembly 50. The valve assembly 50 may include the dual check valve 80187 sold by Qosina, having a place of business at Ronkonkoma, N.Y. The valve assembly 50 may include various valve portions, including two one-way valves. The two one-way valves may include a one-way valve assembly 52, which may be a first one-way valve assembly, that opens when negative pressure is formed within the valve assembly 50. Negative pressure may be produced when the piston head 26 moves generally in the direction of arrow 36 to allow a flow of material through the one-way valve assembly 52 generally in the direction of arrow 54. The material may flow generally in the direction of arrow 54 through a tubing 56. The tubing 56 may be a flexible tubing to connect with a source container 58 holding or containing a volume or liquid, such as an irrigant liquid.

The source container 58 may be a container, such as an IV bag or other appropriate volume of an irrigation fluid. The irrigation fluid may be a selected material such as saline. The irrigation fluid may further include various therapeutic reagents such as antibacterial, antimicrobial, anti-inflammatory, analgesic, hemostatic, and wound healing components.

The tubing 56 may be connected with a connector 60 to a connection receptacle 62 of the irrigant volume container. The connector 60 and the connection receptacle 62 can be any appropriate connection members, as is generally understood in the art. The connection of the connector 60 with the connection receptacle 62 may generally be an open connection such that fluid will generally flow from the source container 58 through the tubing 56 once the connector 60 is connected with a connection receptacle 62. The one-way valve assembly 52, however, may control flow of the fluid from the source container 58 to the syringe assembly 24, including within the syringe barrel 32.

Accordingly, as noted above, when the piston head 26 generally moves in the direction of arrow 36, the irrigant is drawn from the source container 58 through the connection receptacle 62 and the connector 60 through the tubing 56 and generally in the direction of arrow 54. The movement of the piston head 26 in the direction of arrow 36 may cause a negative pressure through the connection portion 46 to the valve assembly 50 to open the one-way valve assembly 52. Therefore, the syringe barrel 32 fills with the irrigant fluid.

Once a selected volume of the irrigant is positioned within the syringe barrel 32, however, movement of the piston head 26 in the direction of arrow 36 may be ceased. The piston head 26 may then be moved in the direction of arrow 40 to move the piston head 26 generally towards the connection portion 46 to assist in removing or evacuating the irrigant material from the syringe barrel 32.

When the piston head 26 is moved generally in the direction of arrow 40, the pressure at the valve assembly 50 may be increased. The increased pressure in the valve assembly 50 can close the one-way valve assembly 52 and open a one-way valve assembly 68, which may be a second one-way valve assembly. The increased pressure at the one-way valve assembly 68 may cause the one-way valve assembly 68 to open to allow the irrigant to flow from the syringe barrel 32 through the valve assembly 50 and generally in the direction of arrow 70 through a tubing 72. The tubing 72 may extend along a selected length and may bend according to a selected configuration.

The tubing 72 may be formed of a material that may be rigid or bendable. In various embodiments, the tubing 72 may be bent for use and may maintain the selected bent configuration. Alternatively, or in addition thereto, the tubing 72 may only be flexible and a bendable support structure 74 may be positioned at at least a region of the tubing 72 to assist in supporting and holding the tubing 72 in a selected shape. According to various embodiments, the bendable support structure 74 may be a malleable tube, such as an aluminum tube, fixed within the tubing 72. Various embodiments, may also include malleable wires embedded in a wall of the tubing 72. Further, multiple tubes may be concentrically placed to support a bend. In still further various embodiments, a distal tube may be formed of a second material different from a proximal portion of the tubing 72 that may be malleable. It is understood, however, in various embodiments the tubing 72 may be a single type flexible non-malleable tubing.

The tubing 72 may be bent at a selected radius, such as near a tip 76 to assist in positioning the tip 76 at a selected location. For example, the tip 76 may be selected to be positioned in a sinus cavity, as discussed further herein, and forming a radius or angle near the tip 76 may assist in positioning the tip 76 within the selected sinus. The radius may be supported by the bendable support structure 74 that may be different than the material of the tubing 72.

Figure 2:
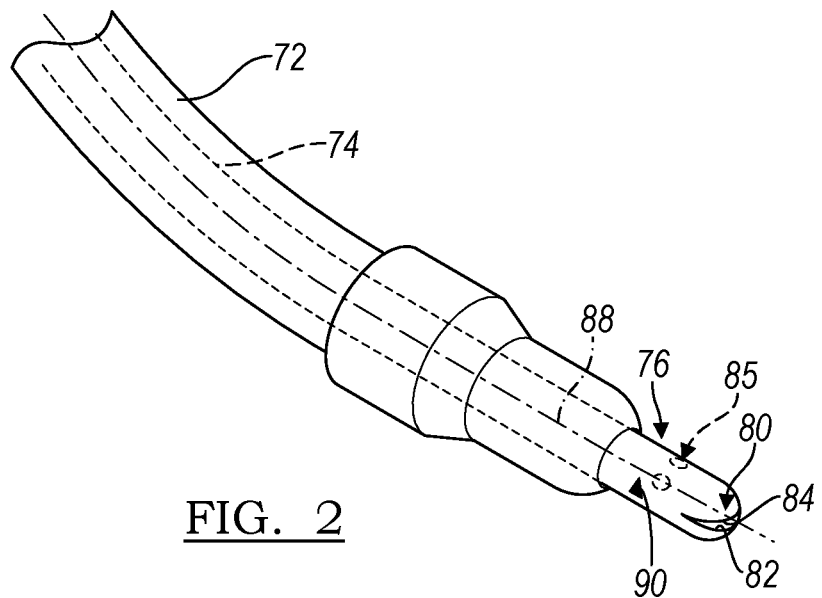
FIG. 2 is a detailed end view of an irrigation nozzle, according to various embodiments.

With continued reference to FIG. 1 and additional reference to FIG. 2, the tip 76 may be formed to cause a selected shape of a spray that exits the tubing 72 and the tip 76. As illustrated in FIG. 2, a detailed view generally along or at the tip 76 of the tubing 72 is illustrated. The tip 76 may include a selectively shaped opening 80. The opening 80 may include a slit that has a first surface 82 and a second surface 84. The first and second surfaces 82, 84 may be angled relative to one another and may include an elongated configuration such that a fan-shaped spray emanates from the tip 76. The opening 80 may also include sidewalls adjacent to the first and second surfaces 82, 84 to further direct the spray. The tip 76 may alternatively to the opening 80 and/or in additional to the opening 80 include one or more holes 85. The holes 85 may be selectively shaped, such as circular, oval, discrete slits, etc.

At the tip 76, the first surface 82 may be angled relative to the second surface 84 to form a selected configuration of the spray, as noted above, which may be a fan shape. Further, due to the angle of the second surface 84, the spray may be directional, such as spraying generally at the angle of the second surface 84 and away from an axis 88 through the tip 76. This can allow the tip 76 to be rotated around the axis 88, such as by rotating the syringe assembly 24, to select a direction of the spray through the opening 80.

The tip 76, as discussed above may include one or more holes 85. If a single one of the holes 85 is included the single hole may direct a stream of the fluid. The single hole may be positioned at any appropriate location around or along the tip 76. Alternatively, there may be many holes 85 positioned at selected locations on the tip 76. For example, the holes 85 may be formed as a ring around an axis 88. The ring of holes may be partial or complete to spray in a selected direction at the tip 76 relative to the axis 88.

Visualization of the location and/or direction of the spray may be made by direct endoscopic or direct visual inspection of the spray. Further, a navigational marker, such as a radiopaque indicator 90 may be included to indicate the location and/or direction of the spray from the opening 80. For example, as illustrated in FIG. 2, a triangle or arrowhead may be the radiopaque indicator 90 that points towards the direction of the spray. Therefore, an imaging may be made to determine the location and/or direction of the spray from the tip 76, such as through the opening 80 and/or the holes 85.

Further, a cross-sectional area or volume of the opening 80 relative to a cross-sectional area of an opening or lumen through the tubing 72 may be selected at an appropriate ratio of about 1:1 to about 1:10,000, including about 1:2 to about 1:100, including about 1:6. Further, more than one of the tips 76 may be provided on the tubing 72. Multiple tips may provide for a spray being directed in a plurality of directions at once. Further, the tips 76 may be selectable or changeable during use. Different tips providing different rations may be used to provide different spray patterns and/or pressures. Accordingly, a kit may be provided that includes the irrigation system 20 with one or more tips 76. The tips may be assembled during use. The kit may be provided in a container that allows sterilization of the kit prior to use. The ratio of the volume of the opening 80 relative to cross-sectional area of the lumen can allow for a selected pressure to be provided through the opening 80. Providing a selected pressure, such as a pressure of about 1 pounds per square inch (PSI) to about 70 PSI may be provided. The selected PSI may assist in a procedure, such as debridement of a region. For example, debridement may include removing a biofilm, breaking an agglomeration, or otherwise providing pressure to an area to assist in removing one or more selected materials (e.g. debris, bacteria, irritant or allergen), or clearing a selected area.

Figure 3:
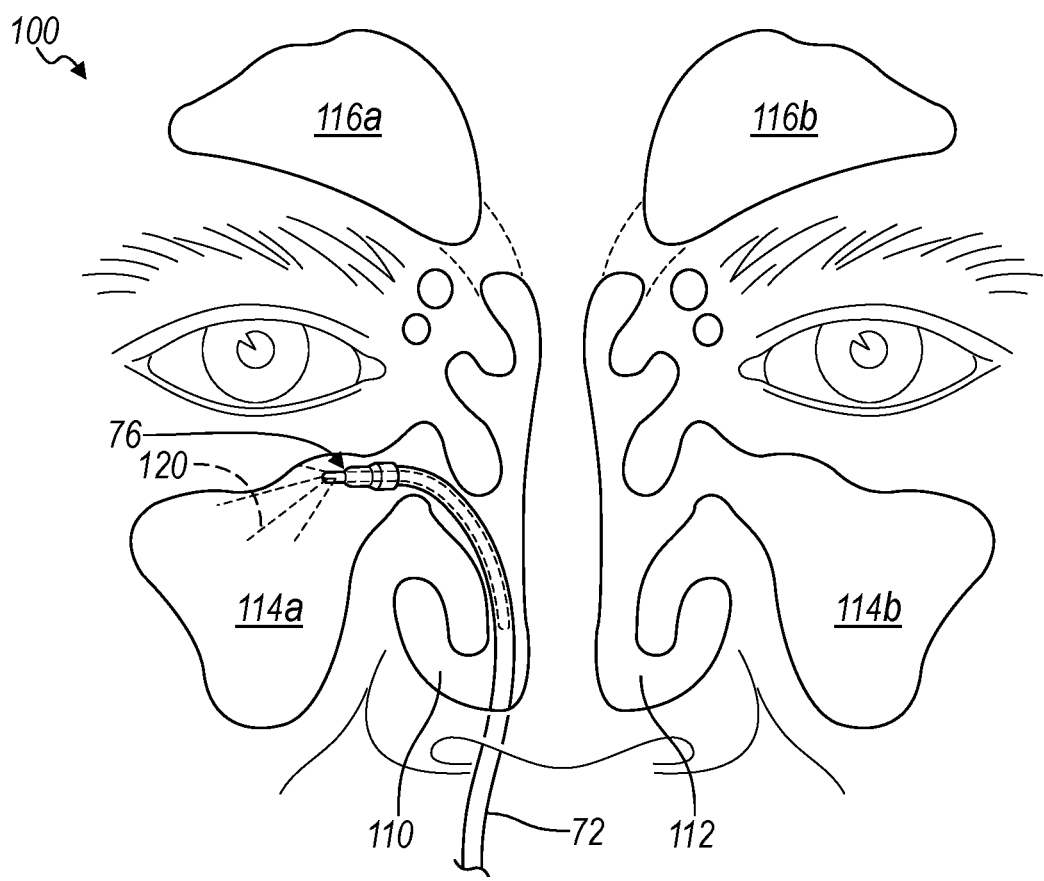
FIG. 3 is a schematic environmental view of an irrigation site.

With continuing reference to FIGS. 1 and 2 and additional reference to FIG. 3, the irrigation system 20 may be used to debride or irrigate a selected nasal passage or sinus cavity. As is generally understood by one skilled in the art, a subject, such as a human subject 100, may include or have a first nasal passage 110 or a second nasal passage 112. Further, the human subject 100 may include one or more sinus cavities including schematically illustrated sinus cavities, including maxillary sinuses 114a and 114b and frontal sinuses 116a and 116b.

During a procedure, the tip 76 may be introduced through the first nasal passage 110 and moved into the maxillary sinus 114a. The tip 76 may be carried on the tubing 72 and may be manipulated into position via holding and operating the syringe assembly 24. During use, the user may then move the piston head 26 generally in the direction of arrow 36 to fill the syringe barrel 32 and then generally in the direction of arrow 40 to express the irrigation material through the tubing 72 and out of the tip 76.

When expressing the irrigation material out of the tubing 72 and tip 76, a spray 120 may be formed as the irrigation fluid impinges upon an internal surface of the maxillary sinus 114a. It is understood that the tip 76 may be moved through either or both of the first and second nasal passages 110, 112 into any of the selected sinus cavities, including either of the maxillary sinuses 114a or 114b, or frontal sinuses 116a or 116b or other sinuses such as the sphenoid or ethmoid sinuses. Nevertheless, the user may operate the syringe assembly 24 to irrigate the sinus cavities and/or nasal passages.

During operation, the user may continuously irrigate using a reciprocating action of the piston head 26. By first moving the piston head 26 generally in the direction of arrow 36, the syringe barrel 32 may be filled and then expressing material by moving the piston head 26 generally in the direction of arrow 40. As noted herein, the repeated movement of the piston head 26 in the direction of the first arrow 36 then the second direction arrow 40 a continuous irrigation may be performed.

The reciprocating motion of the piston head 26 may be manually operated by the user and may not cause a continuously steady stream (e.g. the continuous flow may be pulsatile) during the emptying of the source container 58. However, due to the connection of the syringe assembly 24 to the source container 58 through the tubing 56 and the position of the valve assembly 50, the source container 58 may be emptied or continuously used until debridement or irrigation is complete or the source container 58 is empty. Therefore, the user need not remove the syringe assembly 24 from the irrigation site to refill the syringe assembly 24 during an irrigation procedure, but may maintain the tip 76 at a selected irrigation position during an entire irrigation procedure while manually operating the syringe assembly 24 during the irrigation procedure.

It is understood that the irrigation assembly, according to various embodiments, as discussed herein, may be use to irrigate selected surfaces or volumes. FIG. 3 is merely exemplary of irrigating a surface or cavity within a human subject. It is understood, however, that other cavity within a subject may be irrigated. Further, devices, such as implants or treatment devices may have the irrigant applied to their surfaces before, during, or after positioning with in a subject. For example, an implant may have its surface irrigated after implantation to assist in removing an infection, etc.

Figure 4:
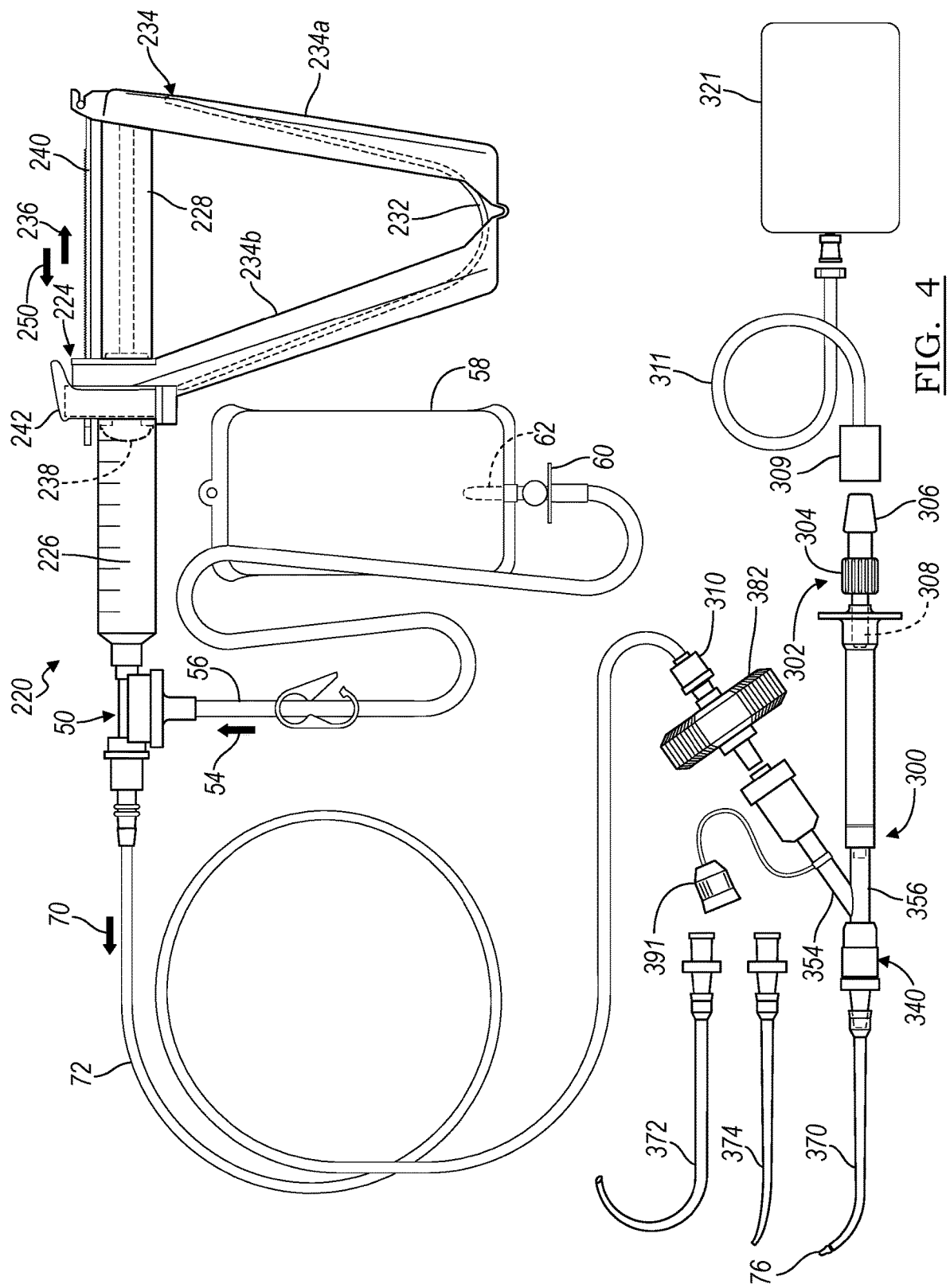
FIG. 4 is a plan view of an irrigation system, according to various embodiments.
Figure 5:
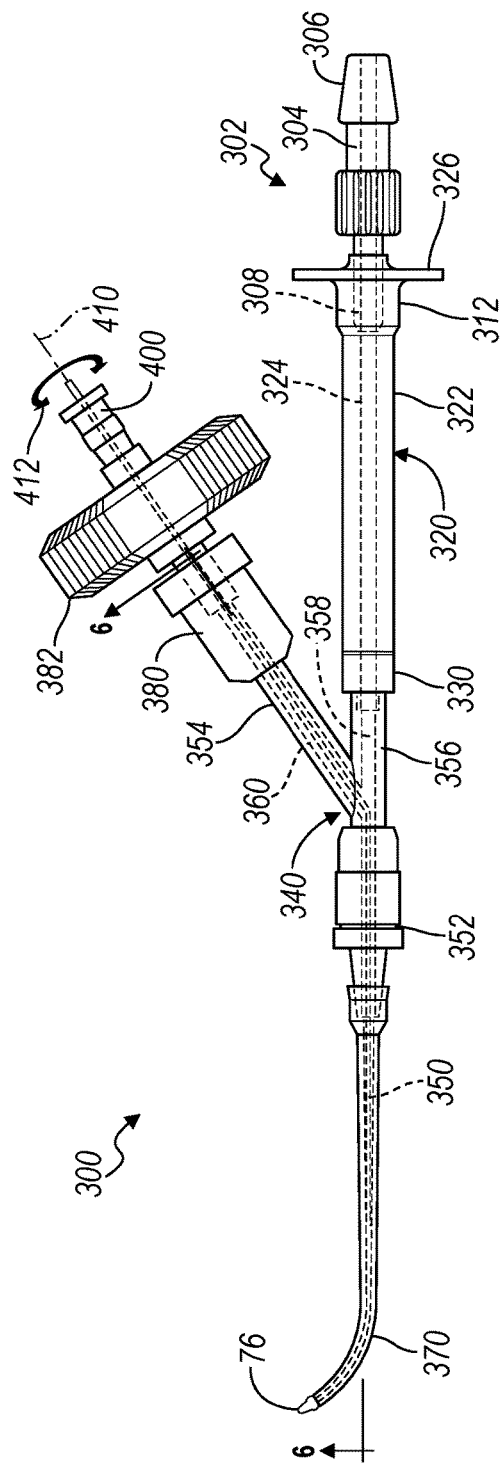
FIG. 5 is a detailed view of an irrigation tip assembly, according to various embodiments.
Figure 6:
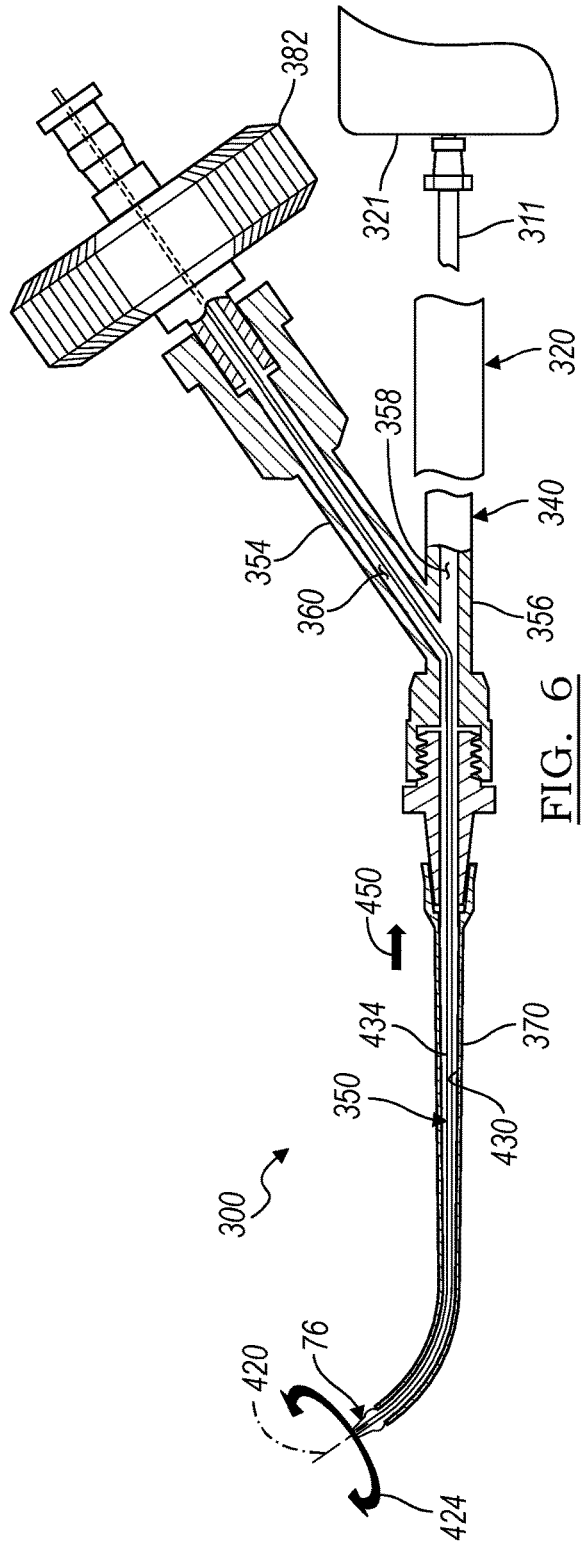
FIG. 6 is a further detailed view of an irrigation tip assembly, according to various embodiments.

An irrigation system 220, according to various embodiments, is illustrated in FIG. 4, FIG. 5, and FIG. 6. The irrigation system 220 is a manual irrigation system that is configured to be powered by a user. For example, a user may apply manual pressure to operate the irrigation system 220. Further, the irrigation system 220 may include components similar to the irrigation system 20, discussed above. Identical components to the irrigation system 20 will be given the same reference numeral in the irrigation system 220 and not discussed in detail below.

The irrigation system 220 may include a syringe system or assembly 224. The syringe assembly 224 may be operated by one or more hands of a user as a manual pump to express or spray an irrigant from the syringe assembly 224. The irrigant may be the same as that discussed above, and may be sprayed into various portions of the human subject 100, as discussed above and illustrated in FIG. 3. It is understood, however, that the irrigation system 220 may be used to irrigate any selected volume and the irrigation of a human patient is not required.

The syringe assembly 224 may be similar to the BD Cornwall™ disposable syringe system, sold by Becton, Dickinson & Co., having a place of business in Franklin Lakes, N.J., USA. The syringe assembly 224 may include a syringe barrel 226 and a syringe plunger 228. As discussed herein, the syringe barrel 226 may operate as a pump barrel having a volume and the syringe plunger 228 may be a plunger for a pump. Connecting the syringe barrel 226 and the syringe plunger 228 may be a spring member 232. The spring member 232 may be held within a casing or handle 234. The spring member 232 may be any appropriate biasing member or system to apply a bias force to the handle 234 and/or the syringe plunger 228.

The spring member 232 may be formed of a selected material, such as a metal or metal alloy, that causes it to be biased to an expanding or open position. Thus, the spring member 232 may be a biasing member that biases the handle 234 and/or the syringe plunger 228. In biasing the syringe plunger 228, the spring member 232 may bias and/or draw the syringe plunger 228 generally in the direction of arrow 236 to move a plunger head 238 in a first direction in the syringe barrel 226. By moving the syringe plunger 228 in the direction of arrow 236, a pressure in the syringe barrel 226 may be reduced so that it may be filled with a fluid from the source container 58. The spring member 232, therefore, biases the syringe assembly 224 to assist in filling the syringe barrel 226 and generally towards a full position. The handle 234 may further include a stopping or an arresting strap 240 that connects to a stop member or portion 242. The stop member or portion 242 is configured to engage a fixed portion of the syringe barrel 226 or is fixed to the syringe barrel 226. The arresting strap 240 engages the stop member or portion 242 to limit travel of the handle 234 when biased by the spring member 232.

The irrigant may be manually expressed from the syringe assembly 224 by the user grasping the handle 234 and squeezing or pressing a first handle member 234a towards the syringe barrel 226 and towards a second handle member 234b generally in the direction of arrow 250, which may be opposite the direction of the arrow 236. In squeezing the handle 234, the user moves the syringe plunger 228 in a second direction in the syringe barrel 226, and generally in the direction of arrow 250. This forces a fluid out of the syringe barrel 226 and through the valve assembly 50, connected to the syringe barrel 226. The expressed material is directed, by the valve assembly 50, through the tubing 72.

Once a selected material has been expressed or emptied from the syringe barrel 226, the user may release or stop squeezing the handle 234. Once the handle 234 is released, the spring member 232 in applying the biasing force, will cause the handle 234, connected to the syringe plunger 228, to generally move in the direction of arrow 236. The spring member 232 may be configured and manufactured to overcome any force applied by the first handle member and the second handle member 234a, 234b, alone, and friction of the syringe plunger 228 within the syringe barrel 226. In this manner, the syringe barrel 226 may be refilled with an irrigant from the source container 58 as the spring member 232 biases the handle 234 in the direction of arrow 236 to move the syringe plunger 228 in the direction of arrow 236. The spring member 232, therefore, may also make continuous or extended irrigation easier and less stressful to a user. The biasing spring may provide all of the force necessary to refill the syringe barrel 226. Thus, the user may only need to provide the force to express material from the irrigation system 220. As noted herein, expressing material may be performed by the user squeezing the handle 234.

The source container or source container 58 may be connected with the syringe barrel 226 via or with tubing, such as flexible tubing 56. The source container 58 may hold any selected irrigation fluid, such as those discussed above including sterile saline or other materials that may include therapeutic agents such as antimicrobials, antibacterials, or the like. Further, the source container 58 may be any appropriate container, such as an IV bag.

The source container 58 may be connected with the tubing 56 using the connector 60 at the connection receptacle 62 with the source container 58. The tubing 56 and connector 60 and connection receptacle 62 may be substantially similar to that discussed above. Further, as material exits the source container 58 it may flow in through the tubing generally in the direction of the arrow 54 through the valve assembly 50. The valve assembly 50 may be similar or identical to the valve assembly discussed above including the check valve 80187 sold by Qosina. The valve assembly 50 may include two one-way valves, as discussed above. Accordingly, the valve assembly 50 may allow material only to flow from the source container 58 into the syringe barrel 226 and not from the syringe barrel 226 into the source container 58. Further, the valve assembly 50 may allow material to be expressed only from the syringe barrel 226 through the irrigation tubing 72 while not allowing material to move through the valve assembly 50 from the irrigation tubing 72 either into the syringe barrel 226 or into the source container tubing 56. Therefore, the valve assembly 50 allows material to be drawn from the source container 58 into the syringe barrel 226 and then expressed and irrigated through the irrigation tubing 72 generally in the direction of arrow 70. The valve assembly 50, however, will generally not allow flow in the directions opposite of arrows 54 and 70.

The valve assembly 50 allows the irrigation system 220 to be used to draw an irrigation material from the source container 58 into the syringe barrel 226 and then express the irrigation material from the syringe barrel 226 through the tubing 72, in a manner similar to that discussed above. The irrigation system 220 may be operated by the user squeezing the handle 234 to empty the syringe barrel 226 (at least a selected amount). The spring member 232 may then bias the syringe plunger 228 out of the syringe barrel 226 generally in direction of arrow 236 to refill the syringe barrel 226 from the source container 58. This operation allows for substantially continuous irrigation by reciprocating the syringe plunger 228 in the syringe barrel 226. The user squeezes the handle 234 to express material and then releases the handle 234 to allow the spring member 232 to move the syringe plunger 228 to refill the syringe barrel 226 for the user to then express more fluid, if selected.

The tubing 72 may be connected to a terminal irrigation assembly or tip assembly 300. The terminal irrigation assembly 300, as illustrated in FIG. 4, FIG. 5, and FIG. 6, may include a vacuum tube connection region 302 that may include a connection member 304 having a proximal male connector 306 and a distal male connector 308. The proximal male connector 306 may be received within a female connector 309 of a vacuum source tube 311. The distal male connector 308 may be received within a proximal connection portion 312 of an irrigation tip holder 320. It is understood, however, that the irrigation tip holder 320 need not be included as a separate or separable member.

The vacuum source tube 311 may be connected to a vacuum source 321. The vacuum source may be any appropriate source, such as a PM61 Power Vac Aspirator, sold by Precision Medical, Inc., having a place of business in Northampton, Pa. The vacuum source may also be a non-portable system such as a constant suction system, such as one generally available in hospitals as a central suction system.

If selected, the irrigation tip holder 320 may include an external wall 322 that defines an internal cannula 324. The suction may be drawn through the internal cannula 324 and the suction or vacuum source tube 311. The irrigation tip holder 320 may be formed from a syringe barrel such as a syringe Luer-Lok® hypodermic syringe sold by Becton, Dickinson and Company Corporation, having a place of business in Franklin Lakes, N.J. The syringe barrel may have the vacuum tube connection region 302 positioned within a proximal end 326 of the syringe barrel that defines the proximal connection portion 312. As discussed herein, therefore, suction may be drawn through the irrigation tip holder 320 at a selected time. The irrigation tip holder 320 may further include a Luer-lok® hypodermic syringe with a partial or half-twist connection at a distal end connector 330. A Y-connector or Y-connection portion 340 may connect with the distal end connector 330. As noted above, the irrigation tip holder 320 need not be included and the vacuum source tube 311 may be connected directly to the Y-connector 340.

The Y-connector 340, as discussed further herein, may communicate with or have an irrigation tip tube 350 passed through at least a portion of the Y-connector 340, including an "Y"-arm or extension 354 extending from a central member 356 of the Y-connector 340. The central member 356 may define a first, main, or central cannula 358 and the Y-arm or extension 354 may also define a second, auxiliary, or extension cannula 360. The central cannula 358 may intersect with the extension cannula 360 and be in fluid communication. The Y-connector 340 may be connected at the distal end connector 330 to the irrigation tip holder 320. As discussed herein, suction may draw material through the central cannula 358 and the internal cannula 324 through the vacuum source tube 311.

The Y-connector 340 connects at a connection region 352 with one or more sheaths that are sheather so the sip tube 350. The tip tube 350 may be sheathed or covered in one or more fixed shape sheaths or sleeves. The sheaths may include a 70° curved sheath 370, a 120° curved sheath 372, and a 13° curved sheath 374. It is understood, however, that more sheaths may be provided and that sheaths of other curvatures may be provided. Each of the sheaths 370, 372, 374 may be passed over the tip tube 350. The tip tube 350 may be flexible enough that it will obtain or be held in the shape of the sheath 370, 372, 374 when placed inside of the sheath 370, 372, 374. Each of the sheaths 370, 372, 374 may be selectively and/or separately connected to the connection region 352. Each of the sheaths may include an outer diameter of about 1 millimeter (mm) to about 10 mm, including about 1 mm to about 6 mm, and further including about 3 mm to about 5 mm.

The tip 76 may extend from the tip tube 350. In various embodiments, the tip 76 may be formed separate from the tip tube 350 and inserted into and connected to the tip tube 350. In various embodiments, the tip 76 may be formed at a distal end of the tip tube 350. The tip tube 350 extends from the tip 76 through a portion of the Y-connector 340 at the connection region 352 and into the extension cannula 360 of the Y-arm or extension 354. The tip tube 350 further extends through an extension arm connector 380 and a directional control system that may include a direction control member (e.g. a grip or handle) 382 to a tip tube connector 400. The tip tube connector 400 may connect with a female connector 310 of the tubing 72. When connected, as material is expressed from the syringe barrel 226, the material may travel past the valve assembly 50 (in the general direction of arrow 70) through the tubing 72 and through the tip tube 350 and the tip 76 to a selected location, such as within a sinus passage as discussed above. Therefore, material may be irrigated through the tip 76 of the irrigation tip tube 350 from the syringe barrel 226.

The tip tube 350 may be fixedly connected to the direction control member 382 which may rotate within the extension arm connector 380. As the direction control member 382 rotates, such as around an axis 410 in the direction of double headed arrow 412, the tip tube 350 may also rotate causing the tip 76 to also rotate. As the tip 76 rotates it may be rotated around an axis 420 that may be defined by the tip tube 350 and the selected sheath positioned over the tip tube 350, such as the sheath 370 as illustrated in FIGS. 5 and 6.

As discussed above, the tip 76 may include the opening 80 that forms a fan or other selected shape of the spray of the material being expressed through the tip or from the tip 76. In rotating the direction control member 382 around the axis 410, which in turn rotates the tip 76 around the axis 420, generally in direction of the double headed arrow 424, allows the fan or other shaped spray to also be rotated around the axis 420. Therefore, if a substantially flat fan is expressed from the tip 76 and the fan rotates around the axis 420, the fan may cover a surface generally defining a circle or disc shape around the axis 420.

Further, the sheath 370 (as may all of the sheaths 370, 372, 374) may include an opening or passage between an internal wall 430 and an outer wall 434 of the tip tube 350. The sheath 370, in forming the passage, will allow the suction or vacuum formed from the vacuum source 321 to be drawn through the sheath 370 and, in turn, through the central cannula 358 of the Y-connector 340 and the internal cannula 324 of the irrigation tip holder 320 and then through the vacuum source tube 311. The suction may be passed the tip 76 and though the selected sheath 370, 372, 374, generally in the direction of arrow 450.

As discussed above, the vacuum source 321 may be a constant vacuum source providing a constant vacuum and suction through the terminal irrigation assembly 300. Thus, suction may always be provided at or near the tip 76 through the sheath, such as the sheath 370, even during expressing or irrigation of a selected area. In providing constant suction or vacuum, the irrigation material may not build up at a selected location and removed or debrided material may be withdrawn once it is loosened from a selected surface. Therefore, the terminal irrigation assembly 300 may provide both a suction and irrigation at or near the tip 76 of the terminal irrigation assembly 300.

Accordingly, the irrigation system 220 may be operated to irrigate at the tip 76 and vacuum or suction material near the tip 76 through the sheath 370 (or other appropriate sheath 370, 372, 374) connected to the connection region 352. A user may irrigate an area, such sinus or other selected volume, and material once expressed from the tip 76 and/or debrided from a surface may be removed with the suction.

It is understood that the irrigation system 220 may be operated in performing a procedure on a human, such as for irrigation of the nasal passage or sinus cavity. It is further understood, however, that irrigation system 220 may be used in a non-human subject for irrigating, providing a selected material (e.g., a lubricant) or cleaning a selected volume of any appropriate object. For example, the irrigation system 220 may be used to provide a selected liquid to a machine system for a selected purpose, including those expressed above.

In addition, the user may remove the syringe assembly 224 from the Y-connector 340 and place a cap or other member 391 in its place. The cap 391 may be tethered to the Y-connector 340 or otherwise obtained to block the irrigation passage of the Y-connector 340. When blocked, the vacuum source 321 would provide the only flow through the Y-connector 340 and the system may operate in a suction only mode. Thus, the irrigation system 220 may be blocked to allow only suction, for various purposes.

Figure 7:
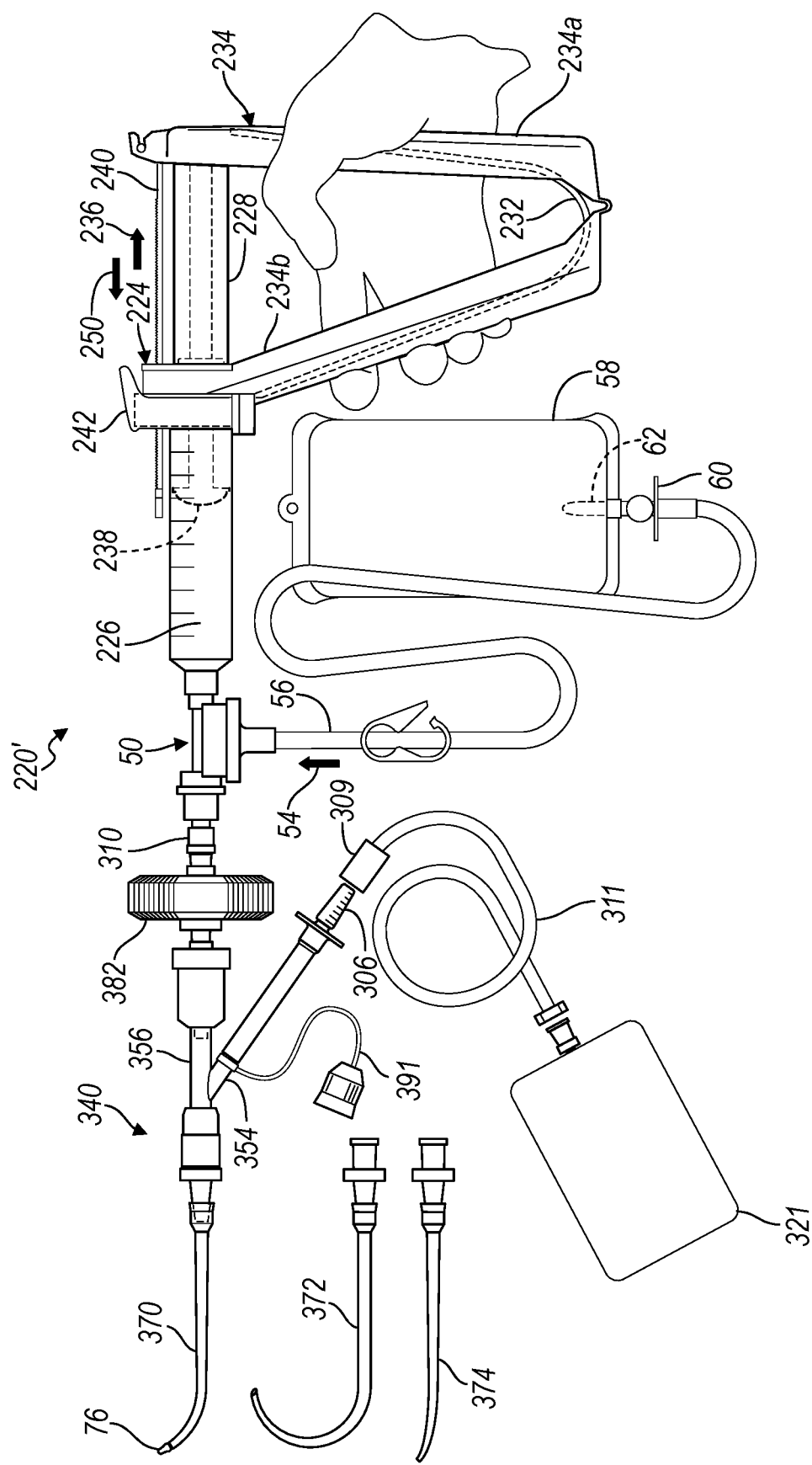
FIG. 7 is a plan view of an irrigation system, according to various embodiments.

According to various embodiments an irrigation system 220', as illustrated in FIG. 7, may be altered relative to the irrigation system 220 illustrated in FIG. 4 above. The irrigation system 220' illustrated in FIG. 7 may include the syringe assembly 224 connected to the Y-connector 340 without the tubing 72 between the syringe assembly 224 and the Y-connector 340. The syringe assembly 224 may be connected to the Y-connector 340 through the female connector 310 and the direction control member 382. Therefore, the direction control member 382 may be still operated to change direction of the tip 76 by moving the tip tube connector 400, as discussed above.

Further, as illustrated in FIG. 7, the irrigation system 220' may have the syringe assembly 224 connected to the central member 356 rather than to the Y-arm or extension 354 as illustrated in FIGS. 4, 5, and 6. It is understood that this is not required, but that the Y-connector 340 may be connected in either manner for the irrigation system 220, illustrated in FIG. 4, or the irrigation system 220', illustrated in FIG. 7. In the irrigation system 220', however, the cannula 358 through the central member 356 is not operated as the suction cannula, but is the irrigation cannula. Further, the extension cannula 360 in the Y-arm or extension 354 is not the irrigation cannula, but is the suction cannula. Therefore, the cannula in either the central member 356 or the Y-arm or extension 354 is determined by which portion to which it is connected.

In this manner, the irrigation system 220' may be operated with a substantially single hand (as illustrated in FIG. 7) of the user or operator without requiring the user to hold the syringe assembly 224 in one hand and the terminal irrigation assembly 300 in a separate hand. The user, therefore, may be able to move the tip 76 with the sheath 370 by moving the syringe assembly 224 rigidly connected to the sheath 370 through the Y-connector 340. The user may further be able to operate or rotate the tip tube connector 400 with the direction control member 382, as discussed above. Nevertheless, the syringe assembly 224 may be rigidly connected to the terminal irrigation assembly 300 to assist in efficiently operating the irrigation system 220' without the need for the separate tubing 72. The irrigation system 220', however, may operate substantially similar to the irrigation system 220 as described above without the tubing 72. That is, upon squeezing the handle 234, the syringe plunger 228 may move in the direction of arrow 250 to move the irrigation fluid generally in direction of arrow 70 through the terminal irrigation assembly 300 and the tip 76 to irrigate a selected location.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A system for irrigation of a selected location, comprising:
a manual pump assembly having a pump barrel that defines a volume within the pump barrel, and includes a connection portion extending from an end of the pump barrel and configured to connect to a valve assembly;
the pump barrel configured to be connected to a fluid source;
a tip having a tip opening to deliver a selected pressure spray of a fluid through the tip opening to a surface at the selected location;
the valve assembly configured to (i) be connected at the connection portion and (ii) control flow from the fluid source to the pump barrel and from the pump barrel to the tip;
a tip tube having a tip passage, wherein the tip extends from a terminal end of the tip tube; and
a tip sheath having an outer wall and forming an internal passage, wherein the tip tube is rotatably positioned within the internal passage to rotate relative to the tip sheath, wherein the internal passage is configured to direct a suction from near the tip between an internal wall of the tip sheath and an outer wall of the tip tube, while there is irrigation through the rotatable tip tube;
wherein the manual pump assembly is configured to be powered and operated by a user to at least express fluid from the pump barrel;
wherein the manual pump assembly is configured to be reciprocally operated by the user to irrigate the selected location with the fluid through the tip passage and tip opening.

2. The system of claim 1, further comprising:
a plunger moveable within the pump barrel between a first barrel end and a second barrel end;
a biasing system to apply a biasing force to bias the plunger towards the first barrel end;
wherein the user overcomes the biasing force of the biasing system to irrigate the selected location by moving the plunger towards the second barrel end.

3. The system of claim 2, wherein the valve assembly includes:
a first one-way valve configured to control flow from the fluid source to the pump barrel; and
a second one-way valve configured to control flow from the pump barrel to the tip.

4. The system of claim 3, wherein the valve assembly is coupled directly to the pump barrel;
wherein the first one-way valve opens when the plunger moves toward the first pump barrel end and the second one-way valve opens when the plunger moves toward the second pump barrel end.

5. The system of claim 4, wherein the internal passage of the tip sheath includes an elongated portion and a curved portion;
wherein the tip tube conforms to a selected configuration of the internal passage.

6. The system of claim 5, further comprising:
a Y-connection portion having a first cannulated section and a second cannulated section; and
a direction control member coupled to the first cannulated section;
wherein the tip tube rotatably extends through the first cannulated section and is rotatable by the direction control member.

7. The system of claim 6, further comprising:
a vacuum tube connected to the second cannulated section;
a constant suction source;
wherein the suction is operable to be formed at or near the tip through the second cannulated section and the internal passage and the constant suction source is operable to provide a constant suction.

8. A system for irrigation of a selected location, comprising:
a manual pump assembly having:
a pump barrel defining a pump barrel volume between a first barrel end and a second barrel end, and including a valve connection portion;
a plunger moveable within the pump barrel, and
a biasing system to apply a biasing force to bias the plunger towards the first barrel end;

a fluid source tube configured to fluidly interconnect a fluid source of a fluid and the pump barrel;

a tip assembly having a tip with an opening to deliver a selected material from the pump barrel;

a valve assembly configured to (i) be connected to the valve connection portion and (ii) control flow from the fluid source to the pump barrel and from the pump barrel to the tip of the tip assembly; and a direction control grip member spaced apart from the manual pump assembly;

wherein the tip assembly includes:
- a flexible tip tube extending from and fixed to the direction control grip,
- a tip sheath through which the flexible tip tube extends and rotates relative to the tip sheath, wherein the tip sheath is configured to have a suction drawn therethrough past the flexible tip tube and directed from the tip while the fluid is expressed from the rotatable flexible tip tube, and
- the tip axially held and extending from the flexible tip tube;

wherein the direction control grip member is rotatable relative to the pump barrel to rotate the rotatable flexible tip tube and the tip around an axis of the tip assembly;

wherein the manual pump assembly is configured to be reciprocally operated by a user by applying a user force to overcome the biasing force to move the plunger towards the second barrel end and stopping application of the user force to allow the biasing force to move the plunger towards the first barrel end.

9. The system of claim 8, wherein the valve assembly includes:

a first one-way valve configured to control flow from the fluid source tube into and out of the pump barrel, and a second one-way valve configured to control flow from out of the pump barrel;

wherein the fluid is controlled by the valve assembly to flow only from the fluid source tube into the pump barrel when the plunger moves towards the first barrel end and only from the pump barrel to the tip when the plunger moves towards the second barrel end;

wherein the valve assembly is connected at the second barrel end of the pump barrel.

10. The system of claim 9, further comprising:

a handle having a first handle portion connected to the plunger and a second handle portion connected to the pump barrel; and a spring member coupled to and between the first and second handle portions and an arresting strap coupled to the first handle portion and the pump barrel to limit travel of the handle when biased by the spring member;

wherein the handle is configured to receive the user force to assist the user in overcoming the biasing force by the user squeezing the first handle portion towards the second handle portion;

wherein the manual pump assembly is configured to be held and manually operated by the user to provide the user force with a hand;

wherein the manual pump assembly is configured to be reciprocally operated to allow for continuous delivery of the fluid.

11. The system of claim 10, wherein the tip includes the opening that is configured to form the fluid exiting the tip into a fan shape.

12. The system of claim 11, wherein the tip assembly further includes:

a Y-connector having a first passage to receive the flexible and rotatable tip tube and a second passage forming a suction passage;

wherein the flexible tip tube delivers fluid through the tip, while the suction passage provides the suction near the tip.

13. The system of claim 8, wherein the tip assembly further includes:

a Y-connector having a first passage to receive the rotatable tip tube and a second passage forming a suction passage, wherein the rotatable tip tube delivers fluid through the tip, while the suction passage provides the suction near the tip.

14. The system of claim 13, wherein the valve assembly includes:

a first one-way valve configured to control flow from the fluid source to the pump barrel; and a second one-way valve configured to control flow from the pump barrel to the tip.

15. The system of claim 14, further comprising:

a constant suction source;

wherein the tip sheath has a selected configuration and an internal passage;

wherein the flexible tip tube is rotatable and positioned within the tip sheath defining the internal passage between an internal wall of the tip sheath and an outer wall of the flexible tip tube;

wherein the internal passage is configured to provide the suction near the tip during the delivery of the selected material through the tip and the suction is a constant suction via the constant suction source.

16. A system for irrigation of a selected location, comprising:

a manual pump assembly having a pump barrel and a plunger moveable within the pump barrel;

a valve assembly connected to the manual pump assembly and to a fluid source;

a rotatable direction control grip spaced apart from the manual pump assembly; and a tip assembly having a tip with an opening to deliver a selected material from the pump barrel;

wherein the tip assembly includes:
- a rotatable flexible tip tube extending from and fixed to the rotatable direction control grip, the tip axially held and extending from the rotatable flexible tip tube, and a plurality of tip sheathes, each tip sheath having a different shape and defining an internal passage, wherein the rotatable flexible tip tube extends through and is rotatable relative to each internal passage of each tip sheath;

wherein the rotatable direction control grip is configured to be rotated relative to the pump barrel to rotate the rotatable flexible tip tube and the tip about an axis of the tip assembly;

wherein the manual pump assembly is configured to be operated by a user to irrigate the selected location with a fluid through the opening of the tip;

wherein each of the plurality of tip sheathes is further configured to have a suction drawn through the internal passage while the fluid is expressed from the rotatable flexible tip tube.

17. The system of claim 16, wherein the tip assembly further includes:

a Y-connector having a first passage to receive the rotatable flexible tip tube and a second passage forming a suction passage;

wherein the rotatable flexible tip tube delivers fluid through the tip, while the suction passage provides a suction near the tip.

18. The system of claim 17, wherein the opening in the tip is configured to deliver a fan shaped spray and upon rotation of the rotatable direction control grip, the fan shaped spray correspondingly rotates about an axis of the rotatable flexible tip tube.

\* \* \* \* \*

UNITED STATES PATENT AND TRADEMARK OFFICE
CERTIFICATE OF CORRECTION

PATENT NO. : 11,964,094 B2
APPLICATION NO. : 17/480862
DATED : April 23, 2024
INVENTOR(S) : Jie Wen Page 1 of 1

It is certified that error appears in the above-identified patent and that said Letters Patent is hereby corrected as shown below:

In the Specification

Column 9, Detailed Description, Line 8, Delete "sip" and insert --tip-- therefor In the Claims Column 12, Line 7, In Claim 1, after "tip", insert --,--

Signed and Sealed this
Fourth Day of March, 2025

Coke Morgan Stewart
*Acting Director of the United States Patent and Trademark Office*